United States Patent [19]

Richards et al.

[11] Patent Number: 4,657,869

[45] Date of Patent: Apr. 14, 1987

[54] SELF-CONTAINED DEVICE FOR CARRYING OUT SPECIFIC BINDING ASSAYS

[75] Inventors: James C. Richards, Wilmington; Robert B. Taylor, Newark, both of Del.

[73] Assignee: E. I. Du Pont de Nemours and Company, Wilmington, Del.

[21] Appl. No.: 611,589

[22] Filed: May 18, 1984

[51] Int. Cl.$^4$ ............................................. A16B 10/00
[52] U.S. Cl. .................................... 435/287; 435/292; 435/295; 435/296; 436/807; 436/810; 422/102; 206/569
[58] Field of Search .............. 435/287, 292, 293, 294, 435/295, 296; 215/6; 206/219, 221, 222, 569; 422/102, 56, 58, 99, 101; 436/807, 810, 528, 529, 530, 531, 532, 533, 534

[56] References Cited

U.S. PATENT DOCUMENTS

| | | | |
|---|---|---|---|
| 2,612,163 | 9/1952 | Norman | 206/222 |
| 3,001,403 | 9/1961 | Edwards | 435/292 |
| 3,163,160 | 12/1964 | Cohen | 435/295 |
| 3,327,710 | 6/1967 | Freeserg et al. | 206/222 |
| 3,783,104 | 1/1974 | Henshilwood et al. | 435/295 |
| 3,918,435 | 11/1975 | Beall et al. | 435/295 |
| 3,923,604 | 12/1975 | Monaghan | 435/295 |
| 3,970,429 | 7/1976 | Updike | 436/807 |
| 4,059,685 | 11/1977 | Johnson | 436/807 |
| 4,066,646 | 1/1978 | LeBlanc, Jr. et al. | 436/810 |
| 4,136,680 | 1/1979 | Southworth | 435/295 |
| 4,175,008 | 11/1979 | White | 206/569 |
| 4,223,093 | 9/1980 | Newman et al. | 435/294 |
| 4,312,950 | 1/1982 | Snyder et al. | 435/295 |
| 4,353,868 | 10/1982 | Joolin et al. | 435/295 |
| 4,409,988 | 10/1983 | Greenspan | 435/295 |
| 4,459,360 | 7/1984 | Marinkovich | 436/810 |
| 4,495,151 | 1/1985 | Ohyama et al. | 436/810 |
| 4,582,811 | 4/1986 | Pucci et al. | 436/810 |
| 4,592,994 | 6/1986 | Mattiasson | 430/810 |

Primary Examiner—Carroll B. Dority, Jr.
Assistant Examiner—H. A. Odar

[57] ABSTRACT

A device is disclosed into which a test solution can be added and at least the first step of a specific binding assay can be carried out. The device comprises a two compartment tube containing a removable rod having at one end a plurality of filaments coated with a specific binding partner for the analyte to be determined.

4 Claims, 4 Drawing Figures

SELF-CONTAINED DEVICE FOR CARRYING OUT SPECIFIC BINDING ASSAYS

BACKGROUND OF THE INVENTION

A major problem in clinical diagnosis is the safe and rapid detection of analytes, especially microbiological pathogens which may be present in clinical samples. Conventional methodology requires collection of the sample and subsequent transportation to the clinical laboratory where the sample is processed. Collection of samples frequently involves contacting tissues, body fluids, biopsy specimens, aspirates, etc., suspected of being infected with microbial pathogens with a cotton swab, immersing the swab into a sterile solution and sending the swab-containing solution to the laboratory for further testing. The laboratory technician must remove the swab from the solution and then inoculate agar plates or tissue culture or use the solution to perform more sophisticated tests such as immunoassay. Removal of the swab from the solution can present a biohazard to the technician. Accordingly, there is a need in the field of clinical microbiology for a test device into which a sample can be introduced at the hospital, doctor's office or patient's bedside and in which initial processing steps can be performed without removal of the sample with its attendant biohazards.

SUMMARY OF THE INVENTION

This need is met in substantial measure by the present invention which is an optionally sterile device for detecting an analyte in a test sample comprising a tube member having an upper and a closed lower end, the tube member being subdivided into an upper and an initially dry lower internal compartment, the compartments being separated by a first breakable seal having extended therethrough a rod member having an upper and lower terminus, the lower terminus initially extending into the lower compartment, the lower terminus having attached thereto means for puncturing the first seal and a plurality of filaments, the filaments having attached thereto a binding partner specific for the analyte, the first seal having the rod extended therethrough being capable of preventing fluid communication between the upper and lower compartments when the puncture means resides initially in the lower compartment, the upper compartment having contained therein a solution for suspending the analyte, the upper end of the tube having disposed thereon a cover having means for introducing the test sample into the upper compartment, the cover further having a second breakable seal having the rod extended therethrough, the device being such that after the sample is introduced into the solution in the upper compartment, the upper terminus of the rod can be pulled away from the tube by a predetermined distance causing the puncture means to break the first seal thereby causing the solution to flow into the lower compartment where the analyte and the binding partner can react to form a complex on the filaments, the device further being such that the rod can then be pulled outside the tube causing the puncture means and filaments to pass through the first seal and to break and pass through the second seal, the broken seals being capable of wringing excess solution from the filaments.

The device of this invention may be optionally made sterile after assembly by a convenient means such as gamma radiation or ethylene oxide gas. The intended purpose of the device includes collection of test samples under sub-optimal field conditions in which device transport and use would be subjected to wide ranges of temperatures, humidities, and potential microbial contamination. Sterile, initially dry reagents in the lower compartment would maintain integrity for longer periods under field conditions.

BRIEF DESCRIPTION OF DRAWINGS

The present invention can be understood further by reference to the drawings in which.

DETAILED DESCRIPTION OF THE INVENTION

Figure 1:
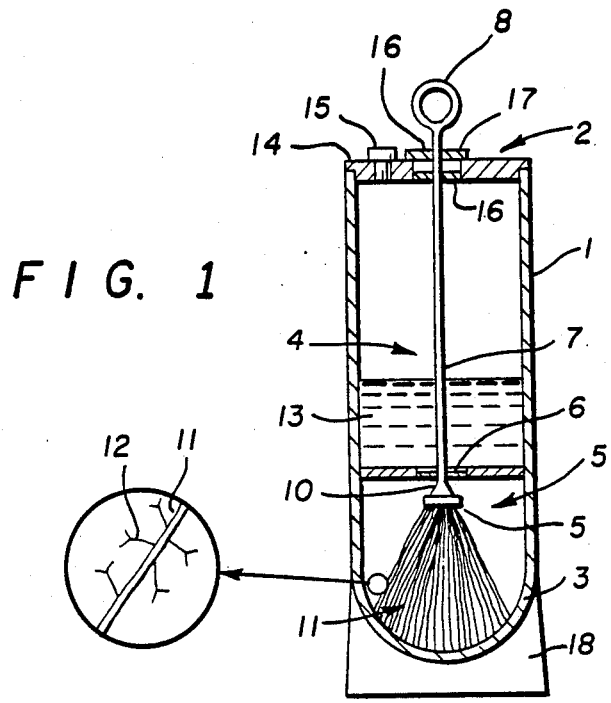
FIG. 1 is a cross-sectional elevational view and FIGS. 2a–2c is a schematic view showing the operation of the device.
Figure 2C:
Figures 2A, 2B:
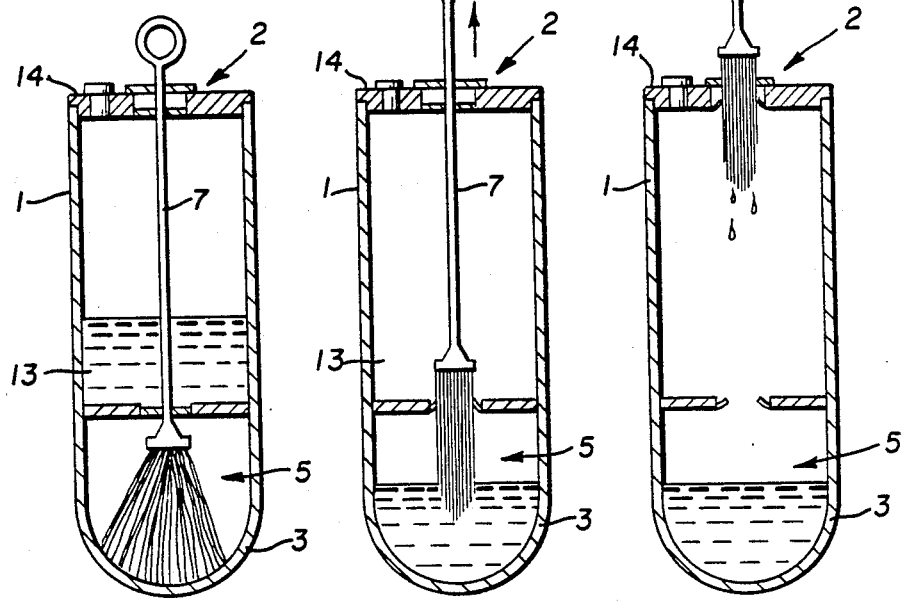

With reference to FIG. 1, the present invention comprises a tube member 1 having an upper end 2 and a closed lower end 3. The tube can be made from a variety of plastics including polypropylene, polyethylene, polycarbonate or high impact polystyrene. The tube 3 is subdivided into an upper internal compartment 4 and an initially dry lower compartment 5. The subdivision can be accomplished by force-fitting one tube inside a slightly larger diameter second tube, thereby subdividing the second tube. Alternatively an extrusion can be made inside a single tube to subdivide the tube into the two internal compartments 4 and 5. The two internal compartments 4 and 5 are separated by a first breakable seal 6 which can extend across the entire inside diameter of the tube or alternatively can extend across a hole in a rigid septum subdividing the tube 1. A suitable material for the first breakable seal 6 in Surlyn ®, a product sold by the DuPont Company, Wilmington, Del. Surlyn ® is a partially neutralized ethylene/-methacrylic acid copolymer. A rod 7 is disposed within the first breakable seal 6. The rod 7 can be made from a rigid or semi-rigid plastic such as polypropylene or high impact polystyrene. The initial disposition of the rod 7 within the seal 6 is such that the seal is capable of preventing fluid communication between the two internal compartments 4 and 5. The rod 7 has an upper terminus 8 which resides outside of the tube 1, and a lower terminus 9 initially disposed in the lower compartment 5. The upper terminus 8 has formed at its end a convenient means for manually grasping the rod 7 for appropriate positioning. The lower terminus 9 has attached thereto means 10 for puncturing the first seal 6 when the rod 7 is pulled outwardly from the tube 1. The puncture means 10 can be an extrusion on the lower terminus 9 of the rod 7 or a rigid collar or similar device. Attached to the lower terminus 9 of the rod 7 below the puncture means 10 are a plurality of filaments 11. The filaments 11 are thin and flexible. Suitable materials are nylon threads and polyethylene terephthalate and polybutylene terephthalate threads. The filaments 11 have attached thereto a binding partner 12 capable of reacting specifically with the substance to be detected referred to herein as the analyte. The use of a plurality of filaments rather than a paddle or dip-stick results in a large surface area to volume ratio which in turn, results in a large excess of binding partner over analyte, thereby increasing the sensitivity of the device. The binding partner 12 should ideally form a strong bond with the analyte to immobilize the analyte on the filaments 11. Additionally, the binding partner 12 should react with the analyte and with no other substance, thereby imparting a high degree of selectivity to the detection device. It is possible to attach more than one binding partner 12 to the filaments 11 so that more than one analyte can be detected in a single device. The upper compartment 4 contains initially a solution 13 into which the analyte is added. For most analytes, the solution 13 can be saline with EDTA (ethylenediaminetetraacetic acid). If the analyte is a bacterium, the solution 13 can contain additionally a sapogenin glycoside, preferably that described by Dorn in U.S. Pat. No. 3,883,425 issued May 13, 1975. The sapogenin glycoside will disrupt host cells releasing soluble antigens into the solution 13. The solution 13 can, in any event, be formulated to optimize the detectability of the analyte for which the test device is to be specific. The binding partner 12 can be attached to the filaments 11 by a variety of techniques including covalent linkage of antibody to nylon by treating partially hydrolyzed nylon with glutaraldehyde or carbodiimide. The binding partner 12 which will be used most frequently in the test device is an antibody molecule which is specific for the analyte of interest. In general, the antibody or other binding partner 12 will be attached to the filaments 11 in an amount capable of binding all of the analyte expected to be present in the test sample. The upper end 2 of the tube 1 has a cover 14 disposed thereon. The cover can be made from polypropylene or polyethylene. The cover 14 has means 15 for introducing the test sample into the upper compartment 4. The sample introduction means 15 can be a port with a snap or a removable plug. The cover 14 also has a second breakable seal 16 through which the rod 7 extends. Like the first breakable seal 6, the second breakable seal 16 having the rod extended therethrough is capable of preventing fluid communication from the upper compartment 4 to the exterior of the device until the seal 16 is punctured by the puncture means 10. Surlyn ® is, again, a suitable material for the second seal. Above the second seal 16 can be placed means 17 for capturing any aerosol created when the rod 7 is pulled completely outside of the device. The aerosol capture means can be an annulus of absorbent material such as reticulated Z-type polyurethane foam (chemically exploded bubble). To help keep the device in a vertical position so that gravity will properly affect operation, a stand 18 can be designed to receive the lower end 3 of the tube 1.

The device operates as follows. The test sample is introduced into the upper compartment 4 by sample introduction means 15. The sample becomes dissolved or suspended in the solution 13 disposed in the upper compartment 4. Rod 7 is pulled away from the tube 1 by a predetermined distance causing puncture means 10 to puncture the first breakable seal 6. The solution 13 containing the analyte will flow into the lower compartment 5 under the influence of gravity. The analyte will bind to the binding partner 12 attached to filaments 11. A time-release capsule comprising appropriate materials known to those skilled in the art such as gelatin, polyvinyl pyrollidone, cellulose acetate phthalate, etc., can be disposed in lower compartment 5 so that upon entry of solution 13, the contents of the capsule will begin to be released slowly. The contents will be a labeled binding partner specific for the analyte. The label is a detectable substance such as a radioisotope, enzyme, chromophore, fluorophore, etc. The labeled binding partner will bind to the analyte which has become immobilized on the filaments 11 by means of binding partner 12. Hence the analyte will be sandwiched between two binding partners, one, binding partner 12, attached to the filaments 11 and the other being the labeled binding partner released from the time release capsule. The amount of label bound to the filaments is related to the amount of analyte present in the sample. Generally, the amount of labeled binding partner present on the filaments 11 will be quantified after the filaments 11 are removed from the solution 13 containing unadsorbed labeled binding partner.

Alternatively, the sample can be introduced into upper compartment 4, the rod 7 can be pulled to puncture seal 6 causing solution 13 to enter lower compartment 5, where analyte will bind to binding partner 12 on filaments 11. The rod 7 can then be fully removed from the device causing puncturing of both seals 6 and 16. As the filaments 11 pass through seals 6 and 16, now broken, excess solution 13 will be wrung from the filaments 11. Aerosol capture means 17 will prevent a biohazard to the operator as the filaments 11 pass through the broken version of second seal 16. The filaments 11 can then be immersed in external wash buffers and detection solutions, the latter containing labeled binding partner to produce a sandwich on the filaments 11 as described above.

The plurality of filaments 11 on the rod 7 results in a high surface area to volume ratio, allowing a vast excess of binding partner 12 to contact the sample analyte.

Because the device of this invention allows processing of sample to being immediately after sample is introduced into the device, the delay normally encountered while sample is en route from patient to clinical laboratory can be used to advantage, namely, to accomplish at least the first step in the clinical analysis: the binding of the analyte to a specific binding partner. Use of this device should result, therefore, in significantly decreased time between sample collection and final clinical determination. The device is equally useful for environmental and food contamination detection.

I claim:

1. A device for detecting an analyte in a test sample comprising a tube member having an upper and a closed lower end, the tube member being subdivided into an upper and an initially dry lower internal compartment, the compartments being separated by a first breakable seal having extended therethrough a rod member having an upper and lower terminus, the lower terminus initially extending into the lower compartment, the lower terminus having attached thereto means for puncturing the first seal and a plurality of filaments, the filaments having attached thereto a binding partner specific for the analyte, the first seal having the rod extended therethrough being capable of preventing fluid communication between the upper and lower compartments when the puncture means resides initially in the lower compartment, the upper compartment having contained therein a solution for suspending the analyte, the upper end of the tube having disposed thereon a cover having means for introducing the test sample into the upper compartment, the cover further having a second breakable seal having the rod extended therethrough, the device being such that after the sample is introduced into the solution in the upper compartment, the upper terminus of the rod can be pulled away from the tube by a distance sufficient to cause the puncture means to break the first seal thereby causing the solution to flow into the lower compartment where the analyte and the binding partner can react to form a complex on the filaments, the device further being such that the rod can then be pulled outside the tube causing the puncture means and filaments to pass through the first seal and to break and pass through the second seal, the broken seals being capable of wringing excess solution from the filaments.

2. The device of claim 1 further comprising means for capturing aerosol when the filaments are pulled through the second breakable seal.

3. The device of claim 1 further comprising a stand into which the lower end of the tube can be inserted thereby maintaining the device in a vertical operating position.

4. The device of claim 1 wherein the means for introducing the sample comprises a port and a removable plug.

* * * * *